US012655528B2

(12) United States Patent
Shin et al.

(10) Patent No.: US 12,655,528 B2
(45) Date of Patent: Jun. 16, 2026

(54) DEVICE FOR PRODUCING AZO COMPOUND

(71) Applicant: DONGJIN INNOCHEM CO., LTD., Siheung-si (KR)

(72) Inventors: Min Seung Shin, Siheung-si (KR); Young Gi Kim, Siheung-si (KR); Sok Kyun Choi, Siheung-si (KR); Su Min Son, Siheung-si (KR)

(73) Assignee: DONGJIN INNOCHEM CO., LTD., Siheung-si (KR)

( * ) Notice: Subject to any disclaimer, the term of this patent is extended or adjusted under 35 U.S.C. 154(b) by 554 days.

(21) Appl. No.: 18/171,363

(22) Filed: Feb. 19, 2023

(65) Prior Publication Data

US 2023/0193482 A1 Jun. 22, 2023

Related U.S. Application Data

(63) Continuation of application No. PCT/KR2021/011051, filed on Aug. 19, 2021.

(30) Foreign Application Priority Data

Aug. 19, 2020 (KR) ........................ 10-2020-0104217

(51) Int. Cl.
*C25B 3/09* (2021.01)
*C07C 245/04* (2006.01)
(Continued)

(52) U.S. Cl.
CPC .............. *C25B 3/09* (2021.01); *C07C 245/04* (2013.01); *C08J 9/103* (2013.01); *C25B 3/07* (2021.01);
(Continued)

(58) Field of Classification Search
CPC ....................................................... C25B 3/09
(Continued)

(56) References Cited

U.S. PATENT DOCUMENTS 3,649,484 A * 3/1972 Prager ...................... C25B 3/23
205/432
6,787,009 B2 * 9/2004 Merk ...................... C25B 11/02
204/268
(Continued)

FOREIGN PATENT DOCUMENTS

CN 1045775 A 10/1990
CN 103657574 A 3/2014
(Continued)

OTHER PUBLICATIONS

Du et al., "Electrochemical dehydrogenation of hydrazines to azo compounds," The Royal Society of Chemistry, 2019, 21(7), 1680-85.
(Continued)

*Primary Examiner* — Harry D Wilkins, III
(74) *Attorney, Agent, or Firm* — United One Law Group LLC; Kongsik Kim; Jhongwoo Peck

(57) ABSTRACT

A device for producing an azo compound includes a reaction unit in which a first solution comprising a hydrazo compound and at least one type of $M_aX_b$; a negative electrode disposed to be in direct contact with the hydrazo compound inside the reaction unit; and a positive electrode disposed inside the reaction unit so as to be in contact with the solution. X is a halogen element, M is at least one selected from the group consisting of hydrogen, Li, Na, K, Mg, Ca, Mn, Fe, Ni, Cu, Ag, Zn, Sn, Zr, and Ti, or at least one selected from the group consisting of a primary ammonium
(Continued)

ion, a secondary ammonium ion, and a tertiary ammonium ion, H is hydrogen, and a and b are each independently any one integer between 1 and 4.

15 Claims, 7 Drawing Sheets

(51) Int. Cl.

| | |
|---|---|
| *C08J 9/10* | (2006.01) |
| *C25B 3/07* | (2021.01) |
| *C25B 3/23* | (2021.01) |
| *C25B 9/17* | (2021.01) |
| *C25B 9/67* | (2021.01) |
| *C25B 15/021* | (2021.01) |
| *C25B 15/08* | (2006.01) |

(52) U.S. Cl.
CPC .................. *C25B 3/23* (2021.01); *C25B 9/17* (2021.01); *C25B 9/67* (2021.01); *C25B 15/021* (2021.01); *C25B 15/083* (2021.01); *C08J 2203/04* (2013.01)

(58) Field of Classification Search
USPC ........................................... 205/432
See application file for complete search history.

(56) References Cited

U.S. PATENT DOCUMENTS

| | | | |
|---|---|---|---|
| 2002/0108852 A1* | 8/2002 | Merk ........................ C25B 3/00 |
| | | | 204/268 |
| 2020/0036037 A1 | 1/2020 | Krause et al. |

FOREIGN PATENT DOCUMENTS

| | | | |
|---|---|---|---|
| CN | 106795105 A | 5/2017 |
| CN | 110923743 A | 3/2020 |
| KR | 10-2013-0114961 A | 10/2013 |
| KR | 10-2014-0058428 A | 5/2014 |
| WO | 2016/068151 A1 | 5/2016 |

OTHER PUBLICATIONS

Wei et al., "Study on the Electro-Oxidizing Preparation of Axobisformamide," Journal of Henan Normal University (Natural Science Edition), vol. 28, No. 4, 370-74.

* cited by examiner (Related Art)

DEVICE FOR PRODUCING AZO COMPOUND

CROSS-REFERENCE TO RELATED APPLICATIONS

This application is a Continuation of International Application No. PCT/KR2021/011051, filed on Aug. 19, 2021, which claims priority to Korean Patent Application No 10-2020-0104217, filed on Aug. 19, 2020. The aforementioned applications are incorporated herein by reference in their entireties.

TECHNICAL FIELD

The present invention relates to a device for producing azo compound, and more specifically, to a device for producing azo compound from a hydrazo compound.

RELATED ART

An azo compound is a compound having R—N=N—R' (azo group) (i.e., a structure in which two nitrogen atoms are double bonded), in which R and R' are each aryl or alkyl. An azo group is a chromophore, and an azo compound including the azo group exhibits colors such as red, orange, and yellow, and thus has a high utility value as a dye and is widely used as a colorant of color filters used in display devices (e.g., liquid crystal display panels, electroluminescence, plasma display panels, etc.).

Meanwhile, azodicarbonamide (ADCA), which is a kind of azo compound, is currently the most commonly used material of foaming agent. The material of foaming agent is an additive for preparing a porous foam by mixing it with a synthetic resin. Azodicarbonamide has a self-extinguishing property and is characterized by non-toxicity, and is used for the purpose of weight reduction, a cushioning property, buoyancy, absorbency, decorativeness, tactility, cost reduction, and dimensional stability of products. Additionally, the foaming of azodicarbonamide is mainly used in polyvinyl chloride (PVC), polyethylene (PE), polypropylene (PP), rubber, an ethylene-vinyl acetate copolymer (EVA), polystyrene (PS), polyurethane (PU), transparent silicone, etc. Additionally, the azodicarbonamide is known as an excellent foaming agent because nitrogen gas is rapidly generated when heated, and decomposition products are non-flammable and non-toxic. Additionally, the azodicarbonamide is also used as a thermostat or bleaching agent for wheat flour (45 ppm or less, US FDA standard).

Meanwhile, azodicarbonamide is usually produced by oxidizing hydrazodicarbon amide (HDCA) with chlorine ($Cl_2$). In particular, a conventional method of producing azodicarbonamide was to directly supply chlorine to reactants (existing method).

However, according to the existing method, an excess amount of chlorine must be used, and since hydrochloric acid (HCl), a strong acid, is produced as a by-product together with azodicarbonamide, there is a problem in that a large amount of alkali compound is required for neutralization of the by-product (wastewater). Accordingly, studies have been focused on the development of a method for generating chlorine ($Cl_2$) by electrolysis. However, this method also had a problem in that it is essential that the positive electrode and negative electrode compartments be separated within a reactor (electrolyzer) through a separator so as to prevent sodium hydroxide (NaOH), a by-product generated in the negative electrode compartment, from decomposing the azodicarbonamide generated in the positive electrode compartment, and a problem in that it requires a large cost for the treatment of the by-product (wastewater), and thus have not been used.

FIG. 1 is a diagram for explaining an electrolysis device and a manufacturing process used for producing an azo compound according to the existing technology.

Referring to FIG. 1, a separator 13 is provided in a container 10, and the container 10 is partitioned into a negative electrode compartment 14 and a positive electrode compartment 15 by a separator 13, the negative electrode 11 is disposed on the negative electrode compartment 14, and the positive electrode 12 is disposed on the positive electrode compartment 15. A stirrer 16 is further provided in the positive electrode compartment 15. A solution 17 containing a hydrazo compound and sodium chloride (NaCl) is put into the container 10, and an azo compound is formed from the hydrazo compound through an electrolysis reaction.

According to the conventional technology of FIG. 1, a method is used where sodium chloride (NaCl) is added to the reactants and chlorine is generated in the reactant through electrolysis and supplied, it is essential that the positive electrode compartment 15 and the negative electrode compartment 14 be separated within a reactor (electrolyzer) [i.e., vessel 10] through the separator 13 so as to prevent sodium hydroxide (NaOH) generated in the negative electrode compartment from decomposing the azodicarbonamide generated in the positive electrode compartment. Since the reaction for producing an azo compound is a slurry reaction, it is essential to stir the reactants for a smooth reaction. The separator 13 is usually formed of a thin membrane, but there is a high likelihood that the separator 13 is damaged by the stirring force of the stirrer 16. Additionally, according to the conventional technology, sodium chloride must be continuously supplied to the reactants so as to continuously produce chlorine that oxidizes the hydrazo compound.

SUMMARY

The technical object to be achieved in the present invention is to provide a device for producing an azo compound, which, in producing an azo compound from a hydrazo compound, does not require continuous input of a chlorine source, etc., can significantly reduce the burden of treatment of wastewater and by-products, and can realize a high conversion rate and a high yield.

Additionally, the technical object to be achieved in the present invention is to provide a device for producing an azo compound, which does not require the use of a separator even if the electrolysis method is used and can reduce power consumption compared to the conventional technology.

The problems to be solved in the present invention are not limited to those mentioned above, and other problems not mentioned will be clearly understood by those skilled in the art from the following description.

According to embodiments of the present invention for achieving the above objects, there is provided a device for producing an azo compound, which includes a reaction unit in which a first solution containing a hydrazo compound and at least one type of $M_aX_b$ is contained; a negative electrode disposed to be in direct contact with the hydrazo compound within the reaction unit; and a positive electrode disposed within the reaction unit so as to be in contact with the solution, wherein: X is a halogen element; M is at least one selected from hydrogen, Li, Na, K, Mg, Ca, Mn, Fe, Ni, Cu, Ag, Zn, Sn, Zr, and Ti, or at least one selected from a primary ammonium ion, a secondary ammonium ion, and a tertiary ammonium ion; the H is hydrogen; and a and b are each independently any one integer from 1 to 4.

The device for producing an azo compound may be configured to produce an $X_b$ molecule by electrolyzing the first solution, and to obtain a second solution containing an azo compound, $M_aX_b$, and HX (wherein H is hydrogen) by oxidizing the hydrazo compound with the $X_b$ molecule produced.

The device further may include a discharge unit connected to the reaction unit to discharge the second solution and separate the third solution comprising $M_aX_b$ and HX therefrom to thereby obtain a solid azo compound.

The device may further include a recycling unit connected to the reaction unit to re-introduce an additional hydrazo compound equivalent to the hydrazo compound and the third solution into the reaction unit.

The $M_aX_b$ may include at least one of a $Cl_2$ precursor and a $Br_2$ precursor.

The negative electrode may be configured to include stainless steel, titanium, aluminum, iron, copper, and Hastelloy, and an alloy or composite material including at least one of these.

The positive electrode may be configured to include titanium, Hastelloy, platinum, stainless steel, gold, silver, iridium, iridium-coated metal, ruthenium, chromium, nickel, manganese, iron, rubidium, or an oxide thereof, graphite, carbon lead, and an alloy or composite material including at least one of them; or configured to include at least one among an electrode where a noble metal is coated on a non-noble metal substrate, an electrode where a noble metal is coated on a non-metal substrate, and a composite-coated electrode of a metal oxide and platinum.

The positive electrode and the negative electrode may consist of multiple pairs.

The device may further include a stirrer for stirring the first solution, in which all of the first solution, the negative electrode, the positive electrode, and the stirrer may be disposed within the reaction unit.

The device may further include a gas treatment unit for capturing gas generated by electrolyzing the first solution, and the gas treatment unit may be disposed at an upper end of the reaction unit.

The reaction unit may include a reaction tank in which the first solution is contained; and an electrode tank in which the positive electrode and the negative electrode are disposed.

The device may further include a pump for circulating the first solution within the reaction tank which includes the reaction unit and the electrode tank.

The device may further include a gas treatment unit, at an upper end of the reactor and the electrode tank, for capturing the gas generated by electrolyzing the first solution.

The device may further include a temperature control unit, which is provided inside or outside of the reaction unit, or as part of the reaction unit to control the internal temperature of the reaction unit.

The device may further include a cooling unit, which is provided inside or outside of the reaction unit, or as part of the reaction unit.

In the device, the first solution, the negative electrode, and the positive electrode satisfy the following Relational Equation (1).

$$0.8 \leq \beta/\alpha \qquad \text{[Relational Equation (1)]}$$

In Relational Equation (1), $\alpha$ is the weight of a first solution (kg), and $\beta$ is the total contact area (cm$^2$) of the negative electrode and the positive electrode in contact with the first solution.

According to embodiments of the present invention, in preparing an azo compound from a hydrazo compound, it is possible to realize an azo compound manufacturing device, which does not require continuous introduction of a chlorine source, etc. using a recycle process by applying a predetermined halogen compound ($M_aX_b$), can remarkably reduce the burden of treatment of wastewater and by-products, and can realize a high conversion rate and a high yield.

Additionally, according to the embodiments of the present invention, even if the electrolysis method is used, it is unnecessary to use a separator, and it is possible to implement a device for manufacturing an azo compound capable of reducing power consumption compared to the conventional technology. Therefore, the manufacturing process and process management can be facilitated, and manufacturing cost can be reduced, and productivity can be improved.

DETAILED DESCRIPTION

Figure 1:
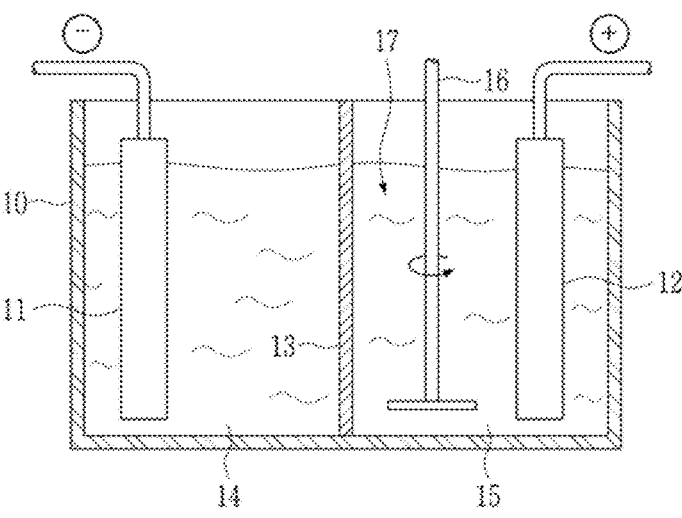
FIG. 1 is a diagram for illustrating an electrolysis device used for producing an azo compound according to the conventional technology and a manufacturing process thereof.

Hereinafter, preferred embodiments of the present invention will be described in detail with reference to the accompanying drawings.

Examples of the present invention to be described below are provided to more clearly explain the present invention to those skilled in the art, and the scope of the present invention is not limited by the following Examples, and the following Examples can be modified into various other forms.

The terms used herein are used to describe specific embodiments, and not to limit the present invention. As used herein, terms in a singular form may include a plural form unless the context clearly dictates otherwise. Additionally, as used herein, the terms "comprise" and/or "comprising" refer to a referenced shape, step, number, action, member, element, and/or existence of these groups and do not exclude the presence or addition of one or more other shapes, steps, numbers, actions, members, elements, and/or groups thereof. Additionally, as used herein, the term "connection" not only means that certain members are directly connected, but also includes indirectly connected members with other members interposed therebetween.

Additionally, as used herein, when a member is located "on" another member, this includes not only a case in which a member is in contact with another member but also a case in which another member is present between the two members. As used herein, the term "and/or" includes any one and any combination of one or more of those listed items. Additionally, as used herein, terms such as "about", "substantially", etc. are used in the meaning of the range or close to the numerical value or degree, in consideration of inherent manufacturing and material tolerances, and are used to prevent the infringer from unfairly using the disclosure, in which the exact or absolute figures are mentioned, provided to help the understanding of the present application.

The size or thickness of the regions or parts shown in the accompanying drawings may be slightly exaggerated for clarity and convenience of description. Like reference numerals refer to like elements throughout the detailed description.

Figure 2A:
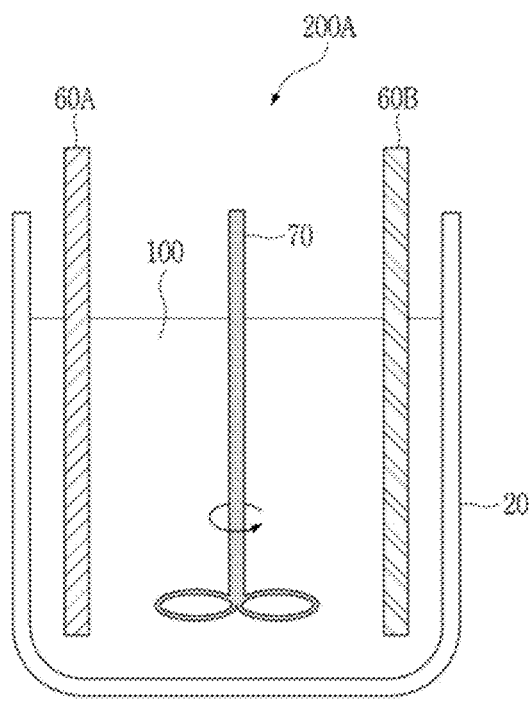
FIGS. 2A, 2B, and 2C are diagrams each showing a device for producing an azo compound according to an embodiment of the present invention.
Figure 2B:
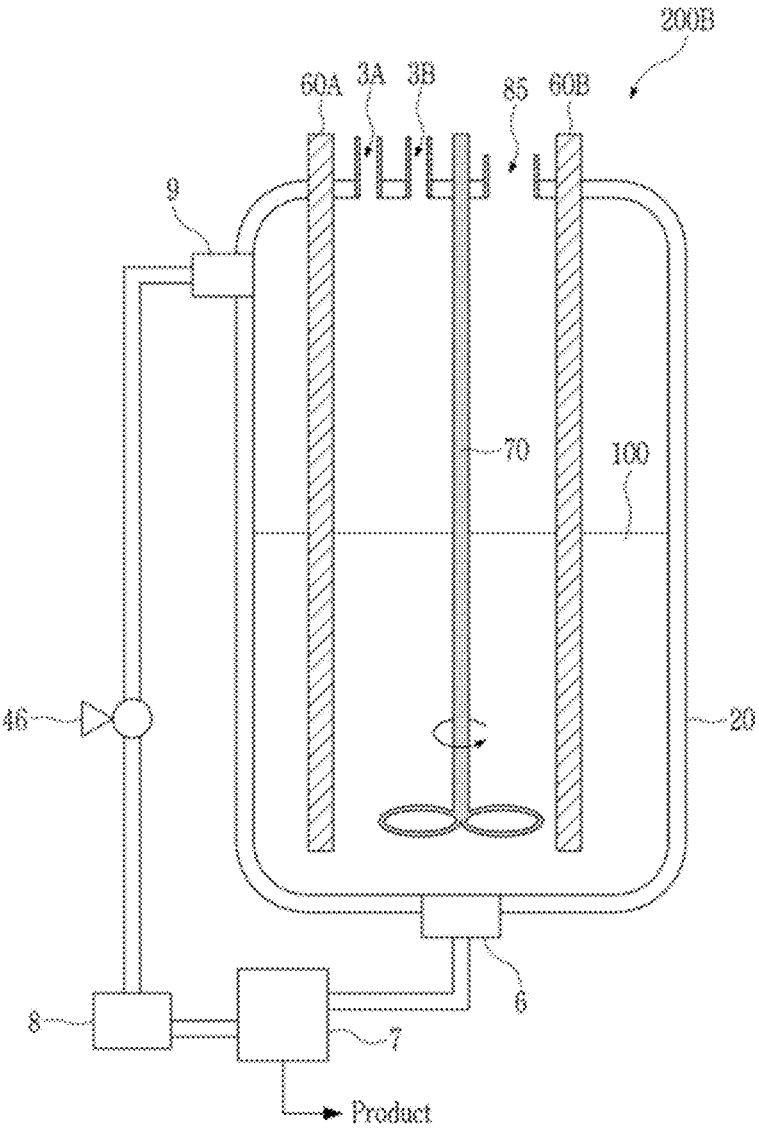
Figure 2C:
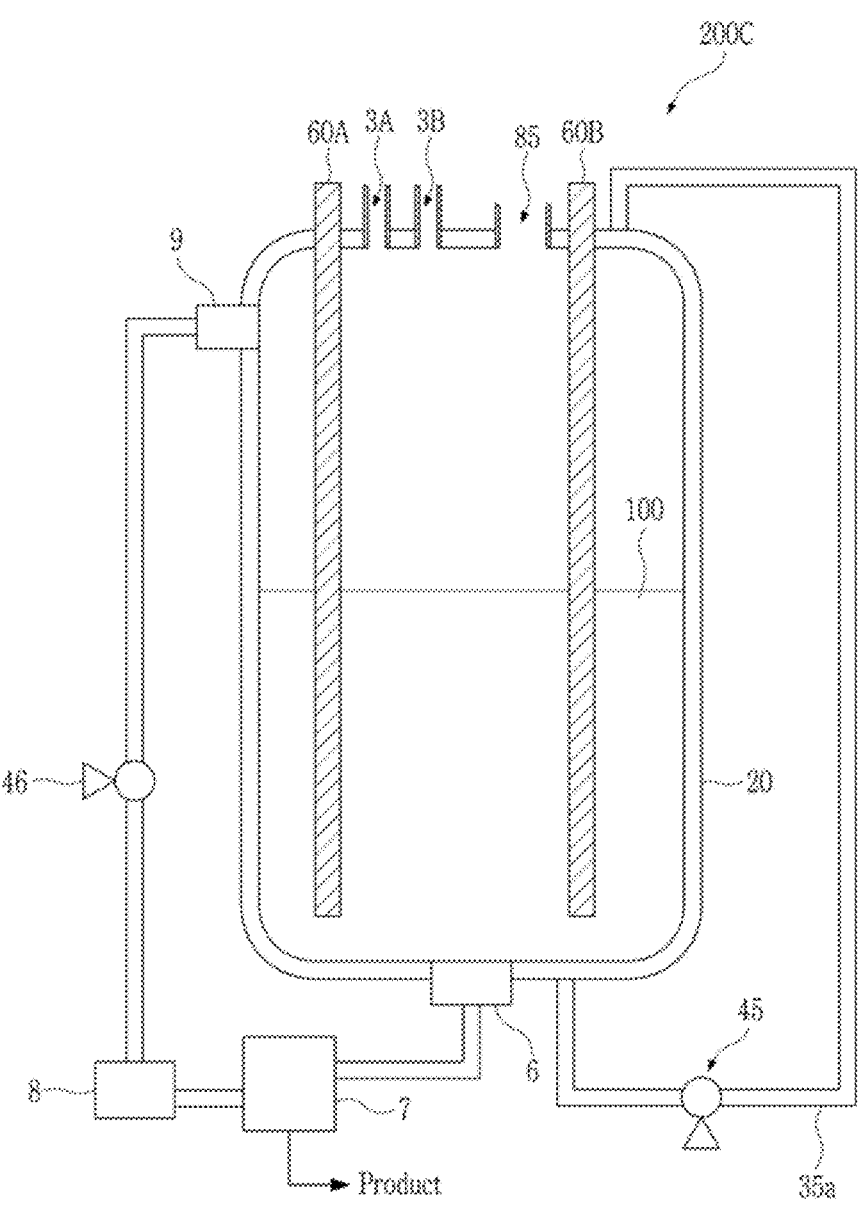

FIGS. 2A to 2C are diagrams each showing a device for producing an azo compound according to an embodiment of the present invention.

Referring to FIGS. 2A to 2C, the device for producing an azo compound according to the embodiment of the present invention may include reaction units 200A to 200C. The reaction units 200A to 200C may include a reaction tank (i.e., a reaction vessel) 20. The solution 100 for preparing an azo compound according to the embodiment may be contained in the reaction tank 20. In particular, the solution 100 may correspond to a solution in any one of the first to fourth steps (S10 to S40), which will be described later with reference to FIG. 5. The solution 100 may be a solution containing at least one kind of $M_aX_b$, and may further include at least one of a hydrazo compound, HX, an azo compound, and a solvent. In particular, the X may be a halogen element. For example, X may include at least one of Cl, Br, and I. The M may be at least one selected from hydrogen, Li, Na, K, Mg, Ca, Mn, Fe, Ni, Cu, Ag, Zn, Sn, Zr, and Ti, or at least one selected from a primary ammonium ion, a secondary ammonium ion, and a tertiary ammonium ion. The ammonium ion may include $NH_4(NH_4^+)$. Meanwhile, the H represents hydrogen, and a and b may each independently be an integer of any one of 1 to 4. Additionally, the solution may further include an additive as necessary. The additive may be at least one selected from the group consisting of sulfuric acid ($H_2SO_4$) and nitric acid ($HNO_3$), and is not limited as long as it is a material capable of serving as an electrolyte by being dissolved in a solution.

The reaction units 200A to 200C may include a negative electrode 60A and a positive electrode 60B disposed in the solution 100. The negative electrode 60A and the positive electrode 60B are for the electrolysis reaction of the solution 100, and at least a portion of them may be disposed in the solution 100. The negative electrode 60A may be disposed to be in direct contact with the hydrazo compound in the reaction units 200A to 200C. The positive electrode 60B may be disposed in the reaction units 200A to 200C to be in contact with the solution 100. The electrolysis reaction may correspond to the electrolysis in the first step (S10) and the fourth step (S40), which will be described later with reference to FIG. 5.

The positive electrode 60B may include at least among titanium (Ti) and alloys thereof, Hastelloy, platinum (Pt) and alloys thereof, stainless steel (e.g., SUS), iridium (Ir) and alloys thereof, iridium (Ir)-coated metals, ruthenium (Ru) or oxides thereof, graphite, and carbon lead. The negative electrode 60A may include at least one among stainless steel (e.g., SUS), titanium (Ti) and alloys thereof, and aluminum (Al) and alloys thereof. However, the materials of the positive electrode 60B and the negative electrode 60A described above are exemplary, and the present application is not limited thereto. As the material of the positive electrode 60B, an electrode where a noble metal (e.g., gold, silver, platinum, ruthenium, etc.) is coated on a noble metal substrate, a minor metal substrate (e.g., titanium, chromium, nickel, manganese, etc.), and a non-noble metal substrate (e.g., titanium, stainless steel, iron, Hastelloy, etc.); an electrode where a noble metal is coated on a non-metal substrate (e.g., olefin resin, engineering resin, a carbon-based substrate, etc.); a composite electrode coated with platinum and a metal oxide (e.g., iridium oxide or ruthenium oxide); the coated electrode as described above by a minor metal; etc. may be used. The materials for the positive electrode and the material of the negative electrode are not limited as long as they are electrode materials that do not cause corrosion even in an acidic solution.

As the shape of the negative electrode 60A or the positive electrode 60B, a plate material, a punched metal with holes, mesh, porous metal, fiber shape, etc. may be used. The process efficiency can be further improved by variously modifying the shape of the negative electrode 60A or the positive electrode 60B to expand the reaction area. However, the shapes of the negative electrode 60A and the positive electrode 60B are not limited to those described above and other various shapes/structures may be used.

The negative electrode 60A and the positive electrode 60B may be formed as a pair, or may be formed of a plurality of pairs of two or more pairs. For the efficiency of the reaction, it may be more advantageous that the distance between the negative electrode 60A and the positive electrode 60B be close. In an embodiment of the present invention, a separator may not be provided between the negative electrode 60A and the positive electrode 60B. Additionally, the method for connecting the negative electrode 60A and the positive electrode 60B may include a series connection, a parallel connection, or a mixed connection of a series connection and a parallel connection, etc., but is not limited thereto.

Meanwhile, the reaction unit of the device for producing an azo compound according to an embodiment of the present invention may be a reaction unit 200A having a structure in which the upper portion of the reaction tank 20 is open as shown in FIG. 2A, and may be a reaction unit 200B having a closed structure as shown in FIG. 2B. When the reaction tank 20 has the reaction unit 200B with a closed structure as shown in FIG. 2B, the reaction tank 20 may further include a discharge unit 6 for discharging reactants/products and a gas treatment unit 85. The gas treatment unit 85 may be provided at an upper end of the reaction tank 20. Various types of gas (e.g., ammonia ($NH_3$) gas, nitrogen ($N_2$) gas, hydrogen ($H_2$) gas, chlorine ($Cl_2$) gas, bromine ($Br_2$) gas, etc.) generated in the process of performing the method for producing an azo compound according to an embodiment of the present invention can be captured and used in a variety of ways.

Additionally, as shown in FIG. 2B, in a configuration for recycling the reactants (a hydrazo compound and a solution containing $M_aX_b$ and HX), a dehydration unit (product filter) 7, a dehydration mother liquor storage tank 8, a reaction solution transfer pump 46, and a recycling unit 9 may be further included.

Referring to FIG. 2B, when the reactants/composites are discharged through the discharge unit 6, the azo compound may be separated through the dehydration unit 7. In particular, the dehydration unit 7 may fulfill centrifugal separation, reduced pressure filtration, etc. that are generally used. The solution (a solution containing $M_aX_b$ and HX) remaining after separation of the azo compound through the dehydration unit 7 may pass through the dehydration mother liquid storage tank 8, and through the dehydration mother liquid storage tank 8, the separated solution is re-introduced into the reaction unit 200B through the recycling unit 9 installed in the reaction unit 200B by the reaction liquid transfer pump 46. In particular, the dehydration mother liquid storage tank 8 and the reaction liquid transfer pump 46 may be disposed in the order shown in FIG. 2B or may be disposed in a reversed order of positions.

A filtration unit may be included as needed. Impurities that may be included in the reactants can be filtered through the filtration unit.

Additionally, the reaction units 200A to 200B may further include a stirrer 70 for stirring a solution 100 as shown in FIGS. 2A and 2B. When the solution 100 is properly stirred using the stirrer 70, the reaction may proceed more smoothly, and the efficiency may be increased. The form of the stirrer 70 shown here is merely exemplary, and various kinds of stirrers (a wing type, a magnetic bar type, etc.) may be used. The appropriate stirring speed (rpm) may vary depending on the type of stirrer 70 selected.

It is also possible not to use the stirrer 70, and as shown in FIG. 2C, when the reaction unit 200C does not include a stirrer, the solution can be stirred using an external power (i.e., the pump 45). In particular, the pump 45 is connected to the reaction unit 200C through the connecting pipe 35a. Additionally, through the connecting pipe 35a as a passage, the solution moves from a lower part to an upper part of the reaction unit 200C, and as a result, the effect of stirring the solution in the reaction unit 200C can be achieved.

The device for manufacturing an azo compound according to the present invention may further include a gas treatment unit 85. The gas treatment unit 85 may be provided at an upper end of the reaction tank 20. Various types of gas (e.g., ammonia ($NH_3$) gas, nitrogen ($N_2$) gas, hydrogen ($H_2$) gas, chlorine ($Cl_2$) gas, bromine ($Br_2$) gas, etc.) generated in the process of performing the method for producing an azo compound according to an embodiment of the present invention can be captured and used in a variety of ways.

The device for producing an azo compound according to an embodiment of the present invention may further include a temperature control unit (not shown) provided inside, outside, or as a part of the reaction units 200A to 200C. The temperature control unit, for example, may be provided to uniformly control the temperature inside the reaction unit (200A to 200C) or to maintain a preset temperature range, and may be provided to maintain a temperature in the range of 10° C. to 80° C., preferably in the range of 10° C. to 45° C. If the temperature of the temperature control unit is below 10° C., the reaction rate may be slow or the reaction may not proceed, whereas if the temperature exceeds 80° C., the azo compound may be decomposed by heat to thereby decrease the yield or quality, and there may be a problem in that the amount of electric power required per weight of the azo compound to be manufactured is significantly increased.

Additionally, the device for producing an azo compound according to an embodiment of the present invention may further include a cooling unit (not shown) provided inside, outside, or as a part of the reaction units 200A to 200C. The cooling unit, for example, can improve the quality of the azo compound by preventing the rapid increase of the temperature of the reaction units 200A to 200C during the electrolysis reaction of the solution 100 by the negative electrode 60A and the positive electrode 60B disposed within the reaction units 200A to 200C or the oxidation reaction of the hydrazo compound, and it may be very advantageous for maintaining the concentration of Br⁻ even after the reaction.

The manufacturing process of an azo compound according to an embodiment of the present invention, which will be described later with reference to FIG. 5, can be performed using a device for manufacturing an azo compound including the reaction units 200A to 200C as shown in FIGS. 2A to 2C. Accordingly, the components of the device for manufacturing an azo compound of FIGS. 2A to 2C and their characteristics/actions will be understood in more detail in connection with specific manufacturing processes to be described later with reference to FIG. 5.

Figure 3:
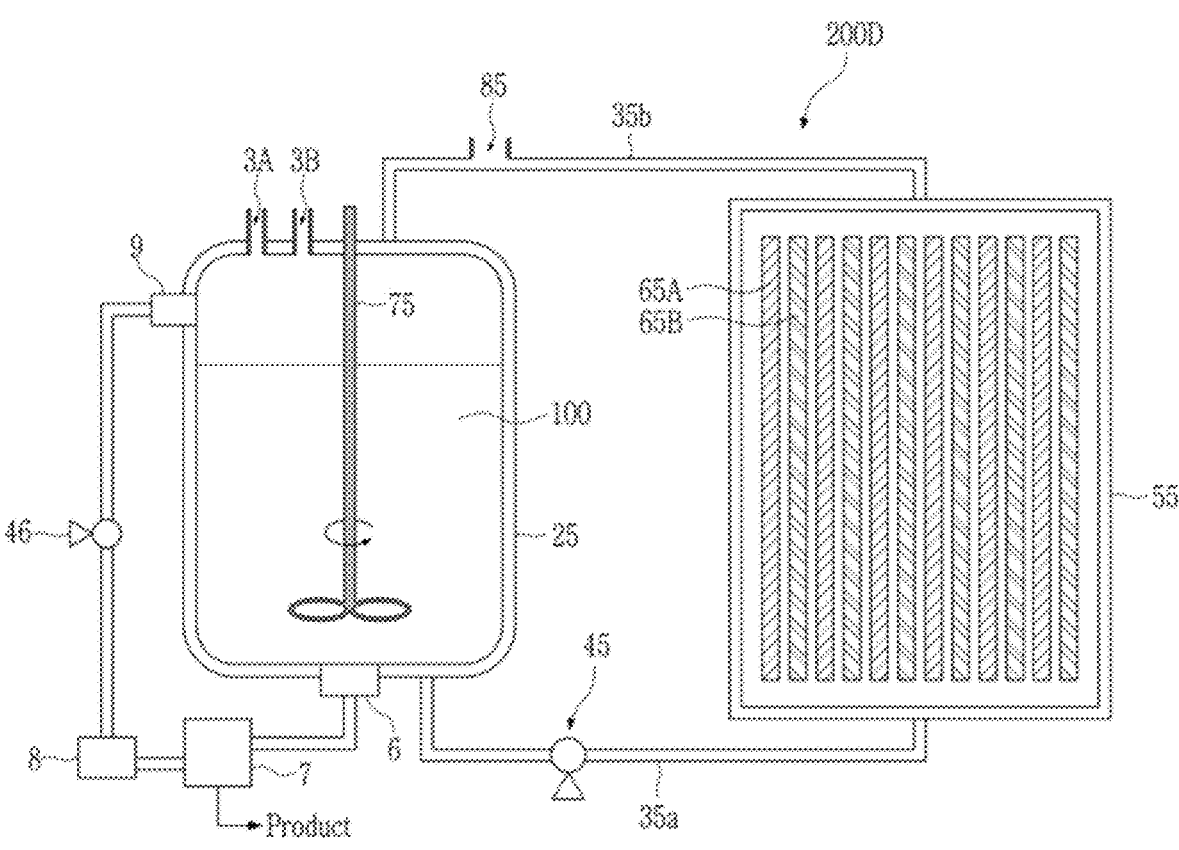
FIG. 3 is a diagram showing a device for producing an azo compound according to another embodiment of the present invention.

FIG. 3 is a diagram showing a device for producing an azo compound according to another embodiment of the present invention.

Referring to FIG. 3, the device for producing an azo compound according to the present embodiment may include a reaction unit 200D. The reaction unit 200D may include a reaction tank (i.e., a reaction vessel) 25. The solution 100 for preparing an azo compound according to the embodiment may be contained in the reaction tank 25. In particular, the solution 100 may correspond to a solution in any one of the first to fourth steps (S10 to S40), which will be described later with reference to FIG. 5. Accordingly, the solution 100 may be a solution containing at least one of the aforementioned $M_aX_b$, and may further include at least one of the above-described hydrazo compound, HX, azo compound, and a solvent.

The reaction tank 25 may be provided with a reaction solution introduction unit 3A for introducing a solution containing $M_aX_b$ and HX, a hydrazo compound introduction unit 3B for introducing a hydrazo compound, and a discharge unit 6 for discharging reactants/composites. The hydrazo compound may be introduced in the form of a slurry. The positions, shapes, structures, etc. of the introduction units 3A and 3B and the discharge part 6 are exemplary and may be changed variously.

Referring again to FIG. 3, the reaction unit 200D of this embodiment may further include an electrode tank (i.e., an electrode chamber) 55 spaced apart from the reaction tank 25. At least one negative electrode 65A and at least one positive electrode 65B may be provided in the electrode tank 55. One or more pairs of negative electrode 65A and positive electrode 65B may be disposed in the electrode tank 55. The negative electrode 65A and the positive electrode 65B are for the electrolysis reaction of the solution 100, and the electrolysis reaction can correspond to the electrolysis in the first step (S10) and the fourth step (S40), which will be described later with reference to FIG. 5. The specific materials of the negative electrode 65A and the positive electrode 65B may be the same as those described with reference to FIGS. 2A to 2C.

The device for manufacturing an azo compound according to the present invention may further include a gas treatment unit 85. The gas treatment unit 85 may be provided at an upper end of the reaction tank 25 and the electrode chamber 55. Various types of gas (e.g., ammonia ($NH_3$) gas, nitrogen ($N_2$) gas, hydrogen ($H_2$) gas, chlorine ($Cl_2$) gas, bromine ($Br_2$) gas, etc.) generated in the process of performing the method for producing an azo compound according to an embodiment of the present invention can be captured and used in a variety of ways.

The reaction unit 200D of this embodiment may further include a connection structure which connects the reaction tank 25 and the electrode tank 55. The connection structure may include, for example, a first connecting pipe 35a and a second connecting pipe 35b. The first connecting pipe 35a may be configured to connect a first end of the reaction tank 25 and a first end of the electrode tank 55, and the second connecting pipe 35b may be configured to connect a second end of the reaction tank 25 and a second end of the electrode tank 55. A pump 45 may be installed in the first connecting pipe 35a. The pump 45 may be a kind of circulation pump. The solution 100 can be circulated within the reaction unit by the operation of the pump 45. In other words, by the operation of the pump 45, the solution 100 moves from the reaction tank 25 to the electrode tank 55 through the first connecting pipe 35_a_, and is then introduced from the electrode tank 55 back into the reaction tank 25 through the second connecting pipe 35_b_.

Additionally, the reaction unit of this embodiment may further include a stirrer 75 for stirring the solution 100 in the reaction tank 25. Various types of the stirrer 75 may be used, and an appropriate stirring speed may vary depending on the type of the stirrer 75.

The manufacturing process of an azo compound according to an embodiment of the present invention, which will be described later with reference to FIG. 5, may be performed using a device for manufacturing an azo compound including the reaction unit 200D as shown in FIG. 3. Accordingly, the components of the device for manufacturing an azo compound of FIG. 3 and their characteristics/actions can be understood in more detail in connection with specific manufacturing processes that will be described later with reference to FIG. 5.

In the case of the reaction unit 200D described in FIG. 3, since the solution 100 may be circulated by the pump 45, the stirrer 75 may not be provided in the reaction tank 25. That is, since an effect similar to that of stirring can be obtained by circulating the solution 100 by the pump 45, the separate stirrer 75 may not be provided.

Figure 4:
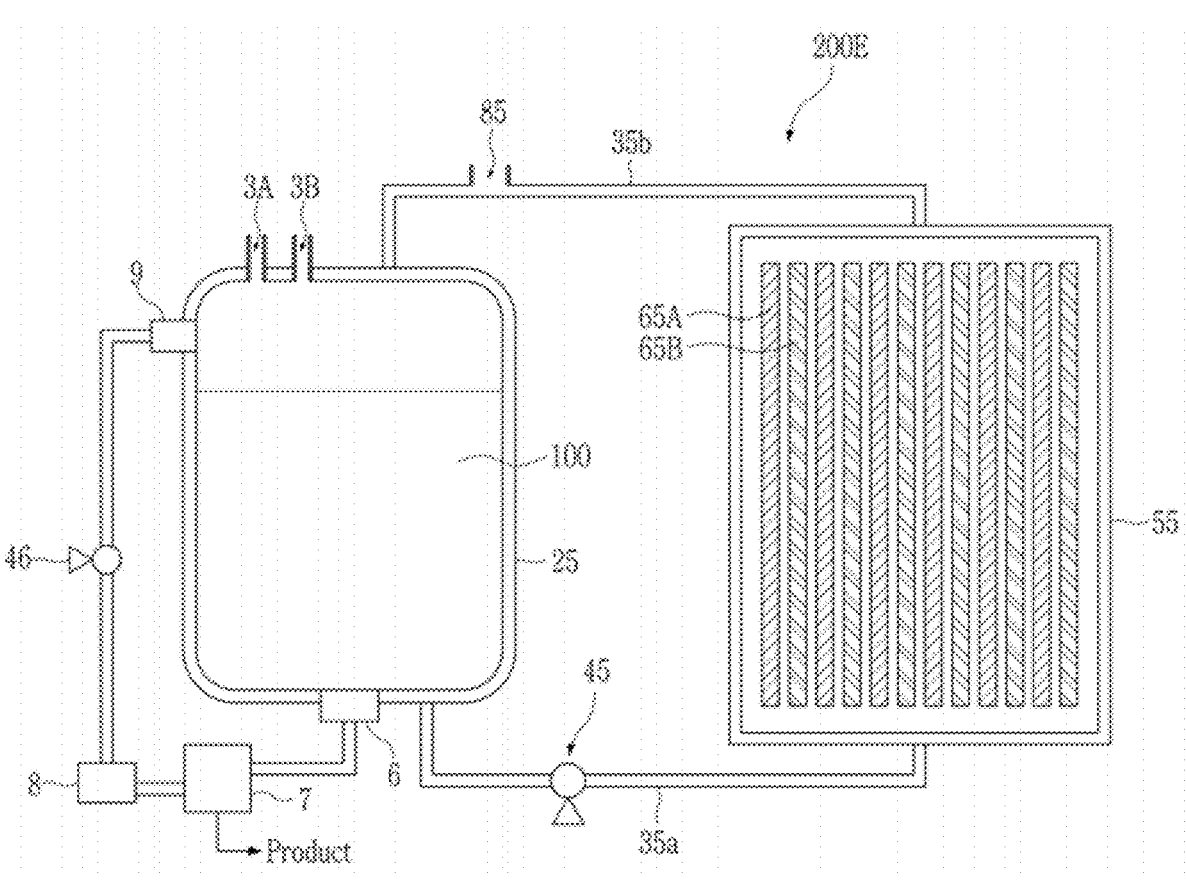
FIG. 4 is a diagram showing a device for producing an azo compound according to another embodiment of the present invention.

The reaction unit excluding the stirrer 75 in FIG. 3 may be the same as shown in FIG. 4. The reaction unit 200E of FIG. 4 may be the same as the reaction unit 200D of FIG. 3 except that it does not include a stirrer.

The device for producing an azo compound according to the embodiments described with reference to FIGS. 2A to 4 may be configured to produce $X_b$ molecules by electrolysis of the first solution containing at least one type of $M_aX_b$, and oxidizing the hydrazo compound with the $X_b$ molecules produced to thereby obtain a second solution containing the azo compound, $M_aX_b$, and HX. Additionally, the device for producing an azo compound may further include a discharge unit (e.g., 6 in FIGS. 3 and 4) connected to the reaction units 200A to 200E so as to discharge the second solution and separate the third solution containing $M_aX_b$ and HX therefrom to thereby obtain a solid azo compound. Additionally, the device for producing an azo compound may further include a recycling unit (e.g., 9 in FIGS. 3 and 4) connected to the reaction units 200A to 200E so as to re-introduce the hydrazo compound (an additional hydrazo compound) equivalent to the hydrazo compound above and the third solution into the reaction units 200A to 200E. The discharge unit 6 and the recycling unit 9, as in FIG. 2B described above, may be connected to a connecting pipe together with the dehydration unit 7, the dehydration mother liquid storage tank 8, and the reaction liquid transfer pump 46. The HX may include, for example, at least one selected from the group consisting of HCl, HBr, and HI. Additionally, the solution containing $M_aX_b$ may further include at least one among a hydrazo compound, HX, an azo compound, and a solvent.

In the device for manufacturing an azo compound, the positive electrodes 60A and 65A may be configured to include stainless steel, titanium, aluminum, iron, copper, Hastelloy, and an alloy or composite material including at least one of them. In the device for producing an azo compound, the positive electrodes 60B and 65B may be configured to include titanium, Hastelloy, platinum, stainless steel, gold, silver, iridium, an iridium-coated metal, ruthenium, chromium, nickel, manganese, iron, rubidium, or oxides thereof, graphite, carbon lead, and an alloy or composite material including at least one of these; or may be configured to include at least one among an electrode where a noble metal is coated on a non-noble metal substrate, an electrode where a noble metal is coated on a non-metal substrate, and a composite electrode coated with a metal oxide and platinum. The materials of the positive electrode and the material of the negative electrode are not limited as long as they are electrode materials that do not cause corrosion even in an acidic solution. The positive electrodes 60B and 65B and the negative electrodes 60A and 65A may consist of one pair or multiple pairs. Additionally, the method for connecting the positive electrodes 60B and 65B and the negative electrodes 60A and 65A may include a series connection, a parallel connection, or a mixed connection of a series connection and a parallel connection, etc., but is not limited thereto.

Electrical energy may be applied to the reaction units 200A to 200E for the above-described electrolysis in the device for producing an azo compound, and the power applied to the reaction units 200A to 200E may be about 1 W to 10 W per 1 g of the azo compound. In particular, the voltage applied to the reaction units 200A to 200E may be about 1.0 V to 13.0 V, specifically, about 2.0 V to 12.0 V. The range of the power and voltage may be at a level relatively lower than the power and voltage used in the device according to the conventional technology described with reference to FIG. 1. Therefore, according to the embodiment of the present invention, it is possible to reduce the amount of electric power consumption and reduce the manufacturing cost compared to the conventional technology. In the above description, the power applied to the reaction units 200A to 200E may refer to the power applied to the positive electrodes 60B and 65B and the negative electrodes 60A and 65A, and similarly, the voltage applied to the reaction units 200A to 200E may refer to the voltage applied to the negative electrodes 60A and 65A.

The device for producing an azo compound according to an embodiment of the present invention may satisfy the following Relational Equation (1), and more preferably satisfy the following Relational Equation (1-1).

$$0.8 \leq \beta/\alpha \qquad \text{[Relational Equation (1)]}$$

$$1.0 \leq \beta/\alpha \qquad \text{[Relation Equation (1-1)]}$$

In Relation Equations (1) and (1-1), $\alpha$ is the weight (kg) of the first solution, and $\beta$ is the total contact area (cm$^2$) of the negative electrode (60A, 65A) and the positive electrode (60B, 65B) in contact with the first solution.

When the numerical value according to Relation Equation (1) is less than 0.8, the yield of the azo compound is significantly lowered and heat is generated in the electrode, and thus the azo compound may be decomposed, thereby causing changes in quality and quality deterioration.

Figure 5:
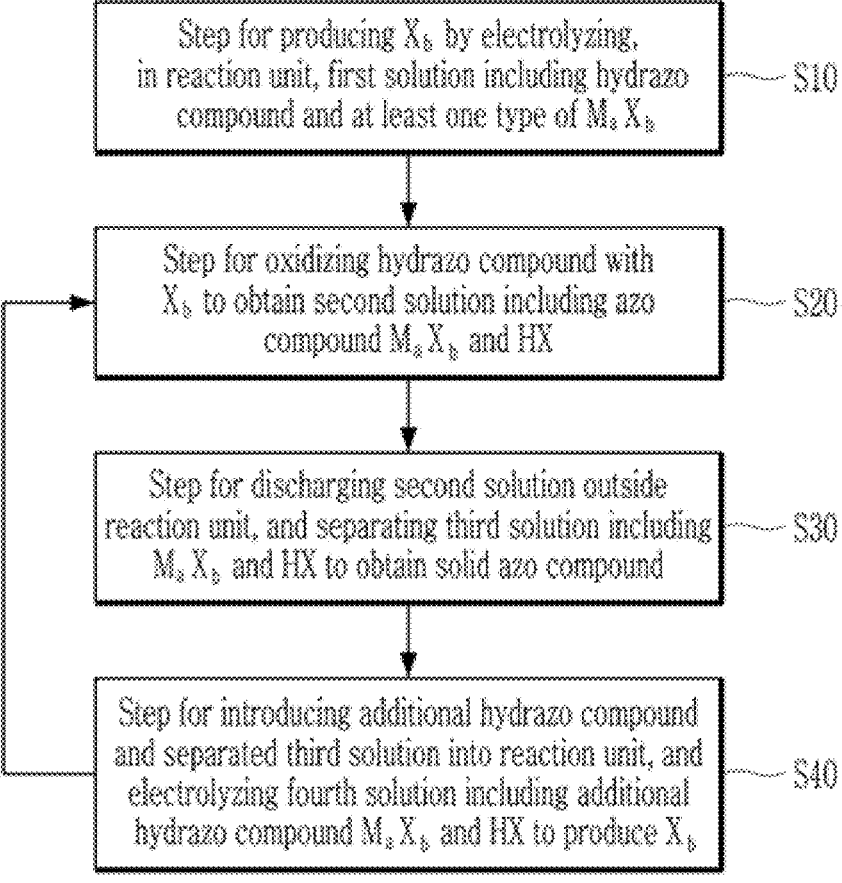
FIG. 5 is a flowchart for illustrating a method for preparing an azo compound according to an embodiment of the present invention.

FIG. 5 is a flowchart for illustrating a method for preparing an azo compound according to an embodiment of the present invention. The method for preparing an azo compound can be performed by referring to FIG. 5 using the device for preparing an azo compound described previously with reference to FIGS. 2A to 4 above.

Referring to FIG. 5, the method for preparing an azo compound according to an embodiment of the present invention may include the following first to fourth steps (S10 to S40).

First step (S10): a step in which a first solution containing a hydrazo compound and at least one kind of $M_aX_b$ is introduced into the reaction unit, and an electrolysis process is performed on the solution so as to produce $X_b$ molecules.

Second step (S20): a step in which the hydrazo compound is oxidized with the $X_b$ molecules produced so as to obtain a second solution containing an azo compound, $M_aX_b$, and HX.

Third step (S30): a step in which the second solution is discharged to the outside of the reaction unit, and a third solution containing $M_aX_b$ and HX is separated therefrom so as to obtain a solid azo compound.

Fourth step (S40): a step in which a hydrazo compound equivalent to the hydrazo compound (an additional hydrazo compound) and the third solution are re-introduced into the reaction unit, and an electrolysis process is performed on a fourth solution containing the hydrazo compound, $M_aX_b$, and HX so as to produce $X_b$ molecules.

Additionally, in the method for producing an azo compound according to the present embodiment, the fourth step (S40), the second step (S20), and the third step (S30) may be regarded as one cycle and the cycle may be performed repeatedly. That is, after the fourth step (S40), a step corresponding to the second step (S20) and a step corresponding to the third step (S30) may be performed, and after performing the step corresponding to the fourth step (S40) again, a step corresponding to the second step (S20) and a step corresponding to the third step (S30) may be further performed. This process can be performed repeatedly. That is, in the case of a batch reaction, the first step (S10), the second step (S20), the third step (S30), and the fourth step (S40) are sequentially performed. In the case of the batch reaction, when the first to fourth steps (S10 to S40) are performed simultaneously, there may be a problem in terms of reaction stability. Additionally, in the case of a continuous reaction, the reaction may be sequentially performed in the order of the fourth step (S40), the second step (S20), and the third step (S30) and simultaneously. In this case, electrical energy can be continuously applied without interruption.

Here, the X may be a halogen element. For example, the X may include at least one of Cl, Br, and I. The M may be at least one selected from hydrogen, Li, Na, K, Mg, Ca, Mn, Fe, Ni, Cu, Ag, Zn, Sn, Zr, and Ti, or at least one selected from a primary ammonium ion, a secondary ammonium ion, and a tertiary. The ammonium ion may include $NH_4$ ($NH_4^+$). Meanwhile, H represents hydrogen, and a and b may each independently be an integer of any one of 1 to 4.

Hereinafter, each of the above steps (S10 to S40) will be described in more detail.

The first step (S10) may be performed such that a first solution containing a hydrazo compound and at least one kind of $M_aX_b$ is introduced into the reaction unit, and an electrolysis process is performed on the first solution to produce $X_b$ molecules. In particular, $M_aX_b$ may be a halogen compound. In an embodiment, the $M_aX_b$ may include any one or more of a $Cl_2$ precursor and a $Br_2$ precursor. For example, the $M_aX_b$ may include a $Cl_2$ precursor alone, a $Br_2$ precursor alone, or include both a $Cl_2$ precursor and a $Br_2$ precursor. In particular, the $Cl_2$ precursor or the $Br_2$ precursor refers to a material capable of providing $Cl_2$ or $Br_2$ through a certain reaction, for example, to a material capable of forming $Cl_2$ or $Br_2$ by an electrolysis reaction. The $M_aX_b$ may be, for example, HCl. This is the case where M is H and X is Cl in $M_aX_b$. Additionally, the $M_aX_b$ may include two or more materials, and may include, for example, HCl and HBr. This is the case where 'M is H and X is Cl' and 'M is H and X is Br' are combined in $M_aX_b$. In the case of a Br-based compound in which X is Br in $M_aX_b$, it is introduced as an electrolyte, but it can also serve as a catalyst. In another embodiment, it may include HCl and NaCl. This is the case where 'M is H and X is Cl' and 'M is Na and X is Cl' are combined in $M_aX_b$. However, the above compounds are exemplary, and other compositions of $M_aX_b$ may be used. Meanwhile, since M may be H, $M_aX_b$ may be the same as HX.

The first solution may include, for example, water as a solvent. However, the type of solvent is not limited to water and may be variously changed. For example, the solvent may include at least one among water, alcohol, and an organic solvent. In the first solution, the hydrazo compound may exist in a slurry state or in a dissolved state. Even if the hydrazo compound exists in a slurry state, the hydrazo compound can be regarded as a partial constitution of a solution or a constitution included in the solution in a broad sense.

In the first step (S10), $X_b$ molecules may be produced by the electrolysis process on $M_aX_b$. The process may be, for example, as shown in Chemical Formula 1 below.

$$M_aX_b \rightarrow M_a + X_b \qquad \text{[Chemical Formula 1]:}$$

During the electrolysis process, $M_a$ may be produced in the negative electrode and $X_b$ may be produced in the positive electrode. If $M_aX_b$ includes HCl, $M_a$ may be $H_2$ (i.e., a hydrogen molecule), and $X_b$ may be $Cl_2$ (i.e., a chlorine molecule). $H_2$ and $Cl_2$ may be gases.

If, M in the $M_aX_b$ is a metal ion or ammonium ion, Chemical Formula 1 may be changed. In a specific example in Chemical Formula 1, when the $M_aX_b$ is 2LiCl, $2Li^+$ and $Cl_2$ gases may be produced by electrolysis, and when the $M_aX_b$ is $2NH_4Cl$, $2NH_4^+$ and $Cl_2$ gases may be produced by electrolysis. Therefore, Chemical Formula 1 above is exemplary, and may vary depending on the material of $M_aX_b$ being used. Additionally, when the solvent of the solution is water ($H_2O$), $2H_2O$ may be decomposed into $H_2$ and $2OH^-$ by electrolysis. In this case, the $2Li^+$ may react with $2OH^-$ to become 2LiOH, and the $2NH_4^+$ may react with $2OH^-$ to become $2NH_4OH$.

The second step (S20) may be performed such that the hydrazo compound is oxidized with the $X_b$ molecules produced to obtain a second solution containing an azo compound, $M_aX_b$, and HX. The reaction in this second step (S20) may be as shown in Chemical Formula 2 below.

$$\text{a hydrazo compound} + X_b \rightarrow \text{an azo compound} + 2HX \qquad \text{[Chemical Formula 2]:}$$

In the hydrazo compound, hydrogen (H) may react with $X_b$ to form 2HX, and the hydrazo compound may be converted into an azo compound.

The second solution obtained through the second step (S20) may be a solution containing the azo compound, $M_aX_b$, and HX. In particular, $M_aX_b$ may be a material remaining after consumption of some of the $M_aX_b$ introduced in the first step (S10). For example, when $M_aX_b$ includes HCl and HBr in the first step (S10), the HBr may simultaneously serve as a catalyst and may remain without being consumed after participating in the reaction, and thus it may remain in the form of $M_aX_b$ in the second step (S20). There is also the possibility that some of the HCl remains. In this regard, it is also possible that the $M_aX_b$ in the second step (S20) corresponds to a part of $M_aX_b$ introduced in the first step (S10). In Chemical Formula 2, when the $X_b$ molecule is $Cl_2$, 2HX may be 2HCl. However, the material of 2HX is not limited to 2HCl and may vary. When the $M_a$ in $M_aX_b$ is H, it may be HX ("first HX"), in which the "first HX" does not refer to HX ("second HX") produced together with the azo compound but refers to an HX different from the "second HX". In the second solution of the second step (S20), the azo compound may exist in a slurry state or in a dissolved state. Even if the azo compound exists in a slurry state, the azo compound can be regarded as a part of a solution or a constitution included in the solution in a broad sense.

The third step (S30) may be performed such that the second solution is discharged to the outside of the reaction unit, and a third solution containing $M_aX_b$ and HX is separated therefrom to obtain a solid azo compound. The second solution obtained in the second step (S20) is discharged to the outside of the reaction unit, and then a third solution containing $M_aX_b$ and HX is separated from the second solution to obtain a solid azo compound. This may be referred to as a dehydration and drying process to obtain a solid azo compound. Through this, a solid azo compound can be obtained, and simultaneously, a third solution containing $M_aX_b$ and HX can be obtained by separation. The solution containing $M_aX_b$ and HX separated in this way may be re-introduced into the reaction unit in a subsequent process to be recycled.

That is, when HX is electrolyzed, $X_b$ molecules are produced, and simultaneously, the $X_b$ molecules oxidize the hydrazo compound to produce an azo compound. Additionally, since HX is produced together with the azo compound as a result of the oxidation reaction, the concentration of HX can be uniformly maintained from the starting time of the second step (S20) to the ending time of the third step (S30). That is, the concentration of the HX in the first to third solutions can be uniformly maintained from the starting time of the first step S10 to the ending time of the third step S30. Therefore, when the solution containing the $M_aX_b$ and HX separated in the fourth step (S40) to be described later is re-introduced after the completion of the third step, the separated solution can be introduced as-is to proceed with the reaction, and it can be re-introduced after replenishing only the amount of the loss occurred in the separated solution.

The fourth step (S40) may be performed such that a hydrazo compound equivalent to the hydrazo compound (an additional hydrazo compound) and the third solution are introduced into the reaction unit, and an electrolysis process is performed on an additional fourth solution containing the hydrazo compound, $M_aX_b$, and HX to produce $X_b$ molecules.

Meanwhile, the term "equivalent" does not mean "the same content" but means "the same compound".

In the fourth step (S40), $X_b$ molecules may be produced by the electrolysis process for the $M_aX_b$ and HX. The process may be, for example, as shown in Chemical Formulas 3-1 and 3-2 below.

$$M_aX_b \rightarrow M_a + X_b \qquad \text{[Chemical Formula 3-1]:}$$

$$2HX \rightarrow H_2 + X_2 \qquad \text{[Chemical Formula 3-2]:}$$

During the electrolysis process, $M_a$ and $H_2$ may be produced in the negative electrode, and $X_b$ and $X_2$ may be produced in the positive electrode. In particular, $X_b$ may include, for example, $Cl_2$. In the case of Chemical Formula 3-1, as described above in Chemical Formula 1, the chemical formula may be changed depending on the material of $M_aX_b$ being used.

The process of producing $X_b$ molecules in the fourth step (S40) may correspond to or be similar to the process of producing $X_b$ molecules in the first step (S10). Accordingly, the fourth step, the second step, and the third step may be regarded as one cycle and the cycle may be performed repeatedly. After the fourth step (S40), a step corresponding to the second step (S20) and a step corresponding to the third step (S30) may be performed, and after performing the step corresponding to the fourth step (S40) again, a step corresponding to the second step (S20) and a step corresponding to the third step (S30) may be further performed. This process may be performed repeatedly.

For example, when HCl is used as a precursor of chlorine ($Cl_2$), the HCl is electrolyzed to produce chlorine ($Cl_2$) and simultaneously the chlorine ($Cl_2$) oxidizes the hydrazo compound. As the hydrazo compound is converted into an azo compound through an oxidation reaction, HCl is produced again. Therefore, the concentration of HCl introduced at the starting time of the reaction of the first step does not change even though the electrolysis and oxidation reactions are performed repeatedly. That is, the azo compound produced at the ending time of the reaction in the third step and the solution obtained by separating the azo compound can be reused.

Additionally, the separated azo compound may include a trace content of a reaction solution containing HCl, and a water washing process may be performed using a large content of water to remove the trace content of the reaction liquid. The low concentration HCl solution produced through the above process can be concentrated again to a high concentration and reused in the electrolysis reaction of the present invention. The above-described HCl is merely described as an embodiment, and is not limited thereto.

According to this embodiment of the present invention, since the third solution separated in the third step (S30) is recycled and used continuously (repeatedly), there is no need to continuously introduce a new halogen source (e.g., a chlorine source), and the burden of treatment of wastewater and by-products can be significantly reduced.

The content of $M_aX_b$ to be initially introduced into the reaction unit in the first step (S10) may be about 1 wt % to about 30 wt % based on the total weight of the first solution. For example, the content of $M_aX_b$ to be initially introduced in the first step (S10) may be about 1 wt % to 20 wt % based on the total weight of the solution containing the hydrazo compound, $M_aX_b$, and HX. When the content of $M_aX_b$ initially introduced into the reaction unit in the first step (S10) is less than 1 wt %, the content of the electrolyte is insufficient and the voltage rises, and thus heat is produced, thereby making it difficult to proceed a substantial electrolysis process, whereas when it exceeds 30 wt %, the acid concentration in the solution becomes thick, and thus the production of an azo compound is prevented, and the electrodes where the electrolysis process proceeds may be damaged. The content of $M_aX_b$ to be initially introduced in in the first step (S10) may be determined in consideration of the total weight of the first solution. The content of $M_aX_b$ to be initially introduced in the first step (S10) may be relatively small. The manufacturing process of an azo compound according to the embodiment may be proceeded using a relatively small content of $M_aX_b$ only in the initial step (i.e., S10).

When the $M_aX_b$ to be introduced in the first step (S10) includes a $Cl_2$ precursor, the content of the $Cl_2$ precursor may be about 3 wt % to 15 wt % based on the total weight of the first solution. When the content of the $Cl_2$ precursor initially introduced into the reaction system in the first step (S10) is less than 3 wt %, the voltage is increased due to insufficient content of electrolyte, and subsequently, heat is produced thereby making it difficult to perform an actual electrolysis process, whereas when it exceeds 15 wt %, the acid concentration in the solution becomes thick, and thus the production of an azo compound is prevented, and the electrodes where the electrolysis process proceeds may be damaged.

When the $M_aX_b$ to be introduced in the first step (S10) includes both the $Cl_2$ precursor and the $Br_2$ precursor, the content of the $Cl_2$ precursor may be the same as described above, and the content of the $Br_2$ precursor may be 0.05 wt % to 5 wt %, preferably 0.1 wt % to 3 wt %, based on the total weight of the first solution. When the content of the $Br_2$ precursor initially introduced into the reaction system in the first step (S10) is less than 0.05 wt %, the decomposition temperature of the azo compound being produced is low, and thus the quality may be significantly reduced, whereas when it exceeds 5 wt %, the production yield of the azo compound may be significantly reduced and the amount of electric power per 1 g of the azo compound may be increased.

Additionally, as long as it is a material capable of producing $X_b$ molecules by electrolysis in the first step (S10), other materials may also be used even if it is not the above-described $M_aX_b$ material.

Meanwhile, the X (a halogen element) in the HX mentioned in the second step (S20), the third step (S30), and the fourth step (S40) may be, for example, at least one of Cl, Br, and I. In other words, the HX may include, for example, at least one selected from the group consisting of HCl, HBr, and HI.

The reaction unit used in the embodiments of the present invention may include a solution containing the $M_aX_b$, a positive electrode to be immersed in the solution, and a negative electrode to be immersed in the solution. In particular, the solution may correspond to the solution in any one of the first to fourth steps (S10 to S40). Accordingly, the solution may further include at least one among a hydrazo compound, HX, an azo compound, and a solvent.

In an embodiment of the present invention, the solution may further include an additive if necessary. The additive may be at least one selected from the group consisting of organic acids or inorganic acids, and is not limited as long as it is a material capable of serving as an electrolyte by being dissolved in a solution.

The positive electrode and the negative electrode may be electrodes for the electrolysis reaction in the first step (S10) and the fourth step (S40). For example, the positive electrode may include at least one among titanium (Ti) and alloys thereof, Hastelloy, platinum (Pt) and alloys thereof, stainless steel (e.g., SUS), iridium (Ir) and alloys thereof, an iridium (Ir)-coated metal, ruthenium (Ru) or oxides thereof, graphite, and carbon lead. The negative electrode may include at least one among stainless steel (e.g., SUS), titanium (Ti) and alloys thereof, and aluminum (Al) and alloys thereof. However, the materials of the positive electrode and the negative electrode mentioned above are exemplary, and the present application is not limited thereto. As the material of the positive electrode, an electrode where a noble metal (e.g., gold, silver, platinum, ruthenium, etc.) is coated on a noble metal substrate, a minor metal substrate (e.g., titanium, chromium, nickel, manganese, etc.), and a non-noble metal substrate (e.g., titanium, stainless steel, iron, Hastelloy, etc.); an electrode where a noble metal is coated on a non-metal substrate (e.g., olefin resin, engineering resin, a carbon-based substrate, etc.); a composite electrode coated with platinum and a metal oxide (e.g., iridium oxide or ruthenium oxide); the coated electrode as described above by a minor metal; etc. may be used. The material of the negative electrode is not particularly limited, and all of the materials exemplified as the material of the positive electrode, general-purpose metals (e.g., iron, copper, and aluminum), stainless steel, Hastelloy, various alloys, and a composite electrode provided with the same may be used. The materials of the positive electrode and the material of the negative electrode are not limited as long as they are an electrode material that do not cause corrosion even in an acidic solution.

The solution around the positive electrode and negative electrode may be "acidic". The pH of the solution in the reaction unit may be uniform or substantially uniform. In the conventional technology, the positive electrode compartment and the negative electrode compartment are separated, and the positive electrode compartment shows the acidity of about pH 1 to pH 4, and the negative electrode compartment shows alkalinity of about pH 11 to pH 14. In contrast, according to an embodiment of the present invention, the pH of the solution in the reaction unit may exhibit a uniform (substantially uniform) acidity as a whole. As the pH of the solution in the reaction unit becomes low, the yield of the azo compound produced may increase and the quality of the azo compound may be excellent. The pH may represent an acidity of about pH 1 to pH 4, specifically, an acidity of about pH 1 to pH 2.

Additionally, in an embodiment of the present invention, the negative electrode may be in direct contact with any one or more of the hydrazo compound and the azo compound. In the conventional device as shown in FIG. 1, in order to prevent decomposition of azodicarbonamide produced in the positive electrode compartment 15, the positive electrode compartment 15 and the negative electrode compartment 14 in the reactor (electrolyzer) (i.e., the vessel 10) must be essentially separated through the separator 13. However, in an embodiment of the present invention, as described with reference to FIGS. 2A to 4, a separator may not be used, and thus, the negative electrode may be in direct contact with any one or more of the hydrazo compound and the azo compound. In this case, since the separator is not used, there are effects in that the manufacturing process and process management can become easier, and there is also an economic advantage in that the separator replacement cost does not occur caused by the breakage of the separator.

In the first step (S10) or the fourth step (S40), electrical energy is applied to the reaction unit for the electrolysis, where the electric power applied to the reaction unit may be, for example, about 1 W to about 10 W per 1 g of the azo compound. In this case, for the completion of an electrolysis reaction, for example, it may take about 4 to 6 hours. In a specific embodiment, when a current of about 10 A is applied per 100 g of the hydrazo compound, it may take about 4 to 6 hours. Additionally, electric energy is applied to the reaction unit for the electrolysis in the first step (S10) or the fourth step (S40), and the voltage applied to the reaction unit may be, for example, about 1 V to 13 V, and specifically, it may be about 2 V to 12 V. The range of the electric power and voltage may be relatively lower than the electric power and voltage used in the device according to the conventional technology described with reference to FIG. 1. Therefore, according to the embodiments of the present invention, it is possible to reduce the electric power consumption and reduce the manufacturing cost compared to the conventional technology.

In the first step (S10), the hydrazo compound may be introduced, for example, in a slurry type. Additionally, before separating the solution containing $M_aX_b$ and HX in the third step (S30), the azo compound may exist, for example, in a slurry state. In this case, there is an advantage in that the hydrazo compound can be more easily converted into the azo compound, and the obtained (synthesized) azo compound can be dehydrated/dried in a relatively simple manner without a complicated process. However, in some cases, the hydrazo compound and/or the azo compound may be in a state dissolved in a solution rather than in a slurry state.

In the method for producing an azo compound according to the embodiments of the present invention described above with reference to FIG. 5, the hydrazo compound may be, for example, hydrazodicarbonamide (HDCA), and the azo compound may be, for example, azodicarbonamide (ADCA). However, these are examples, and the specific materials of the hydrazo compound and the specific material of the azo compound may vary.

Additionally, the method for preparing an azo compound according to an embodiment of the present invention may be performed at a temperature in the range of 10° C. to 80° C., preferably at a temperature in the range of 10° C. to 45° C. In the azo compound manufacturing method, when the temperature is less than 10° C., the reaction rate may be slow or the reaction may not proceed, whereas when the temperature exceeds 80° C., there may be problems in that the azo compound may be decomposed by heat to thereby decrease the yield or deteriorate the quality, and in that the amount of electric power required per weight of the azo compound to be produced may be significantly increased.

The method for producing an azo compound according to another embodiment of the present invention may include the following first to third steps (S10 to S30).

First step (S10): a step in which a first solution containing a hydrazo compound and at least one kind of $M_aX_b$ is introduced into the reaction unit, and an electrolysis process is performed on the solution so as to produce $X_b$ molecules Second step (S20): a step in which the hydrazo compound is oxidized with the $X_b$ molecules produced so as to obtain a second solution containing an azo compound, $M_aX_b$, and HX Third step (S30): a step in which the second solution is discharged to the outside of the reaction unit, and a third solution containing $M_aX_b$ and HX is separated therefrom so as to obtain a solid azo compound The solution around the positive electrode and negative electrode may be "acidic". The pH of the solution in the reaction unit may be uniform or substantially uniform. In the conventional technology, the positive electrode compartment and the negative electrode compartment are separated, and the positive electrode compartment shows the acidity of about pH 1 to pH 4, and the negative electrode compartment shows alkalinity of about pH 11 to pH 14. In contrast, according to an embodiment of the present invention, the pH of the solution in the reaction unit may exhibit a uniform (substantially uniform) acidity as a whole. As the pH of the solution in the reaction unit becomes low, the yield of the azo compound produced may increase and the quality of the azo compound may be excellent. The pH may represent an acidity of about pH 1 to pH 4, specifically, an acidity of about pH 1 to pH 2.

Here, the X may be a halogen element. For example, the X may include at least one of Cl, Br, and I. The M may be at least one selected from hydrogen, Li, Na, K, Mg, Ca, Mn, Fe, Ni, Cu, Ag, Zn, Sn, Zr, and Ti, or at least one selected from a primary ammonium ion, a secondary ammonium ion, and a tertiary. The ammonium ion may include $NH_4$ ($NH_4^+$). Meanwhile, H represents hydrogen, and a and b may each independently be an integer of any one of 1 to 4.

For the specific contents of another embodiment of the present invention, the contents described in the above one embodiment may be equally applied.

EXAMPLES

Hereinafter, an azo compound prepared by the method for preparing an azo compound according to an embodiment of the present invention will be described in detail with reference to Examples and Comparative Examples. Additionally, the Examples shown below are an embodiment to help understanding of the present invention, and the scope of the present invention is not limited.

Method for Producing an Azo Compound

Example 1

A 500 mL beaker, electrodes, hydrazodicarbonamide (HDCA), distilled water, and $M_aX_b$ were prepared for an electrolysis reaction. HDCA, distilled water, and $M_aX_b$ were each weighed and introduced into the 500 mL beaker according to the contents shown in Table 1 below. Thereafter, the introduced materials were sufficiently stirred using a stirrer.

Double boiling was performed in a reactor suitable for the reaction temperature using water, and the mixture was stirred at a temperature corresponding to the experimental conditions through a temperature control unit for 30 minutes to 1 hour to maintain a uniform temperature.

The negative electrode and the positive electrode in the reactor were were installed such that they are in the form to face each other while maintaining a distance of 1 mm to 5 mm, and the facing electrodes are immersed in the solution. In particular, the electrodes were prepared in a structure not to contact with each other and a gap was maintained in a constant state, and the total contact area of the positive electrode and the negative electrode per 1 kg of the solution weight was 2.5 cm$^2$.

Thereafter, the mixture was carefully stirred using a stirrer so that the stirring could be proceeded in a state where no impact was applied to the electrodes. In particular, a turbine-type stirring blade with a diameter of 3 cm was used, and the RPM was maintained at 300 RPM.

The negative electrode and the positive electrode were connected to each electrode immersed in the solution in the reactor using a power supply, and a constant current was supplied to flow. In particular, a condenser was disposed at an upper end of the reactor as a cooling unit.

Upon confirming that all of the reactants were converted into a product, the supply of electricity was stopped and the product was separated using a reduced pressure filter.

Examples 2 to 30 and Comparative Example 1

The preparation was performed in the same manner as in Example 1, but an azo compound was prepared as in Table 1 below.

Regarding the quality of the obtained azodicarbonamide (ADCA) described in Table 1 below, the meanings of the following indications are as follows.

⊡ : It can be used as a high-quality product due to uniform particle shape and particle size.

○: Although the particle shape and particle size are uniform, it is difficult to be used as a high-quality product because it includes materials with some different particle sizes, and it can be used as a general product.

△: The particle shape and particle size are not uniform, and thus it can be used as a product only after separation.

X: The particle shape is poor and the particle size distribution is wide, and thus it cannot be used as a product.

TABLE 1

| | $M_aX_b$ | $M_aX_b$ Content (wt %) | Solvent Content (wt %) | HDCA Content (wt %) | Current (A) | Time (h) | Temperature (° C.) | pH | Yield (%) | Content of ADCA Acquired (g) | Amount of Electric Power per 1 g of ADCA (W/g) | ADCA Quality |
|---|---|---|---|---|---|---|---|---|---|---|---|---|
| Example 1 | HCl | 6 | 69 | 25 | 10 | 1.25 | 40 | 1 | 94 | 23.1 | 1.56 | ◎ |
| Example 2 | NaCl | 6 | 69 | 25 | 10 | 1.918 | 40 | 4 | 82 | 20.2 | 8.71 | ◎ |
| Example 3 | KCl | 6 | 69 | 25 | 10 | 2 | 40 | 4 | 85 | 20.9 | 9.68 | ◎ |
| Example 4 | MgCl₂ | 6 | 69 | 25 | 10 | 1.375 | 40 | 3 | 91 | 22.6 | 6.25 | ◎ |
| Example 5 | HCl | 0.5 | 74.5 | 25 | 10 | — | 40 | 2 | — | — | — | X |
| Example 6 | HCl | 1 | 74 | 25 | 10 | 1.85 | 40 | 1 | 93 | 22.9 | 4.68 | ○ |
| Example 7 | HCl | 3 | 72 | 25 | 10 | 1.5 | 40 | 1 | 93 | 22.9 | 1.9 | ◎ |
| Example 8 | HCl | 15 | 60 | 25 | 10 | 1.333 | 40 | 1 | 92 | 22.5 | 1.59 | ◎ |
| Example 9 | HCl | 17 | 58 | 25 | 10 | 1.333 | 40 | 1 | 88 | 21.625 | 1.66 | ○ |
| Example 10 | HCl | 30 | 45 | 25 | 10 | 1.3 | 40 | 1 | 80 | 19.7 | 1.50 | ○ |
| Example 11 | HCl | 32 | 43 | 25 | 10 | 1.4 | 40 | 1 | 70 | 17.2 | 2.01 | Δ |
| Example 12 | NaCl | 0.5 | 74.5 | 25 | 10 | — | 40 | — | — | — | — | X |
| Example 13 | NaCl | 1 | 74 | 25 | 10 | 2.1 | 40 | 3 | 80 | 19.7 | 2.88 | ○ |
| Example 14 | NaCl | 3 | 72 | 25 | 10 | 2.003 | 40 | 4 | 82 | 20.2 | 2.68 | ○ |
| Example 15 | NaCl | 15 | 60 | 25 | 10 | 2.1 | 40 | 4 | 75 | 18.4 | 3.07 | ○ |
| Example 16 | NaCl | 17 | 58 | 25 | 10 | 3.125 | 40 | 5 | 50 | 12.3 | 6.86 | Δ |
| Example 17 | NaCl | 32 | 43 | 25 | 10 | 3.27 | 40 | 6 | 20 | 4.9 | 17.95 | X |
| Example 18 | KCl | 0.5 | 74.5 | 25 | 10 | — | 40 | — | — | — | — | X |
| Example 19 | KCl | 1 | 74 | 25 | 10 | 2.15 | 40 | 4 | 85 | 20.9 | 9.68 | ○ |
| Example 20 | KCl | 3 | 72 | 25 | 10 | 2.075 | 40 | 4 | 85 | 20.9 | 2.68 | ○ |
| Example 21 | KCl | 15 | 60 | 25 | 10 | 2.15 | 40 | 4 | 75 | 18.4 | 3.14 | ○ |
| Example 22 | KCl | 17 | 58 | 25 | 10 | 3.075 | 40 | 5 | 52 | 12.8 | 6.49 | Δ |
| Example 23 | KCl | 32 | 43 | 25 | 10 | 3.75 | 40 | 6 | 22 | 5.4 | 18.72 | X |
| Example 24 | HCl | 6 | 69 | 25 | 5 | 2.668 | 40 | 1 | 92 | 22.6 | 1.64 | ◎ |
| Example 25 | HCl | 3 | 72 | 25 | 5 | 2.918 | 40 | 1 | 90 | 22.1 | 1.4 | ◎ |
| Example 26 | HCl | 6 | 81.5 | 12.5 | 10 | 0.65 | 40 | 1 | 94 | 11.6 | 1.63 | ◎ |
| Example 27 | HCl | 6 | 54 | 40 | 10 | 2.05 | 40 | 1 | 94 | 37.0 | 1.61 | ◎ |
| Example 28 | HCl | 6 | recycle once | 25 | 10 | 1.25 | 40 | 1 | 94 | 46.2 | 1.56 | ◎ |
| Example 29 | HCl | 6 | recycle 5 times | 25 | 10 | 1.25 | 40 | 1 | 94.5 | 139.4 | 1.56 | ◎ |
| Example 30 | HCl | 6 | recycle 10 times | 25 | 10 | 1.25 | 40 | 1 | 94.5 | 255.5 | 1.56 | ◎ |
| Comparative Example 1 | HCl | 6 | 69 | 25 (urea) | 10 | — | 40 | 1 | 0 | 0 | — | X |

In Table 1, the total mass of the solution containing $M_aX_b$, HDCA, and the solvent is based on 100 g, and the time is based on 25 g of HDCA.

Referring to Table 1, in Examples 1 to 4, in which the type of material for supplying chlorine ($Cl_2$) (i.e., $M_aX_b$) was changed, it was confirmed that although HCl, NaCl, KCl, $MgCl_2$, HBr, etc. are all possible, ADCA of the best quality was obtained in the case of HCl.

In Examples 5 to 23, the content of $M_aX_b$ was changed, and it was confirmed that when the content was less than 1 wt %, ADCA was not produced, whereas when it exceeded 30 wt %, ADCA of low quality was obtained with a yield of 70% or less.

In Examples 24 and 25, the amount of current was changed to be lower than those of other examples, and it was confirmed that although the reaction time was slightly longer, the quality of the ADCA was excellent.

In Examples 26 and 27, the content of HDCA was changed to be lower or higher than those of other examples, and it was confirmed that the quality of ADCA was all excellent regardless of the change in the content of HDCA.

Examples 28 to 30 are results according to the number of reuse of the reaction mother liquor, i.e., a chlorine source and water, recovered in Example 1, and it was confirmed that the yield per cycle of ADCA was the same regardless of the number of reuse.

Comparative Example 1 is a result obtained using urea instead of HDCA, and it was confirmed that no reaction occurred at all.

Examples 31 to 35

An azo compound was prepared in the same manner as in Example 1, except with the values shown in Table 2 below.

Regarding the quality of the ADCA obtained described in Table 2 below, the meanings of the following indications are as follows.

◎: a decomposition temperature of about 207±0.5° C. (expression of an appropriate decomposition temperature)

○: a decomposition temperature of higher than about 207.5° C. to 209.5° C. or below (slightly higher than the appropriate decomposition temperature)

Δ: a decomposition temperature of higher than about 209.5° C. (a decrease of foaming ratio performance due to delayed decomposition)

X: a decomposition temperature of lower than about 206.5° C. (a decreased quality of a foaming body due to premature foaming)

TABLE 2

| | $M_aX_b$ | $M_aX_b$ Content (wt %) | Solvent Content (wt %) | HDCA Content (wt %) | Current (A) | Time (h) | Temperature (° C.) | pH | Yield (%) | Content of ADCA Acquired (g) | ADCA Quality |
|---|---|---|---|---|---|---|---|---|---|---|---|
| Example 31 | HCl | 6 | 68.99 | 25 | 10 | 5 | 40 | 1 | 94 | 1.56 | X |
| | HBr | 0.01 | | | | | | | | | |
| Example 32 | HCl | 6 | 68.9 | 25 | 10 | 5 | 40 | 1 | 95 | 1.43 | ◎ |
| | HBr | 0.1 | | | | | | | | | |
| Example 33 | HCl | 6 | 67 | 25 | 10 | 5 | 40 | 1 | 96 | 1.42 | ◎ |
| | HBr | 2 | | | | | | | | | |
| Example 34 | HCl | 6 | 66 | 25 | 10 | 5 | 40 | 1 | 92 | 1.4 | ○ |
| | HBr | 3 | | | | | | | | | |
| Example 35 | HCl | 6 | 63 | 25 | 10 | 5 | 40 | 1 | 88 | 1.64 | ○ |
| | HBr | 6 | | | | | | | | | |

In Table 2, in Examples 31 to 35, in which the content of HBr (i.e., a $Br_2$ precursor) was changed, it was confirmed that when the $Br_2$ precursor was less than 0.05 wt %, the amount of electric power per 1 g of ADCA was increased, whereas when it exceeded 5 wt %, the yield was lowered while the amount of electric power per 1 g of ADCA was increased.

Examples 36 to 41

An azo compound was prepared in the same manner as in Example 1 except that the control temperature of the temperature control unit was changed as shown in Table 3 below.

Regarding the quality of the ADCA obtained described in Table 3 below, the meanings of the following indications are as follows.

◎ : a decomposition temperature of about 207±0.5° C. (expression of an appropriate decomposition temperature)

○: a decomposition temperature of higher than about 207.5° C. to 209.5° C. or below (slightly higher than the appropriate decomposition temperature)

Δ: a decomposition temperature of higher than about 209.5° C. (a decrease of foaming ratio performance due to delayed decomposition)

X: a decomposition temperature of lower than about 206.5° C. (a decreased quality of a foaming body due to premature foaming)

In Table 3, in Examples 36 to 41, in which the control temperature of the temperature control unit was changed, it was confirmed that the amount of electric power per 1 g of ADCA significantly increased when the adjusted reaction temperature exceeded 80° C.

Examples 42 and 43

An azo compound was prepared in the same manner as in Example 1, but with changes as shown in Table 4 below.

Regarding the quality of the ADCA obtained described in Table 4 below, the meanings of the following indications are as follows.

◎ : a decomposition temperature of about 207±0.5° C. (expression of an appropriate decomposition temperature)

○: a decomposition temperature of higher than about 207.5° C. to 209.5° C. or below (slightly higher than the appropriate decomposition temperature)

Δ: a decomposition temperature of higher than about 209.5° C. (a decrease of foaming ratio performance due to delayed decomposition)

X: a decomposition temperature of lower than about 206.5° C. (a decreased quality of a foaming body due to premature foaming)

TABLE 3

| | $M_aX_b$ | $M_aX_b$ Content (wt %) | Solvent Content (wt %) | HDCA Content (wt %) | Current (A) | Time (h) | Temperature (° C.) | pH | Content of ADCA Acquired (g) | ADCA Quality |
|---|---|---|---|---|---|---|---|---|---|---|
| Example 36 | HCl | 6 | 68.9 | 25 | 10 | 5 | 15 | 1 | 1.57 | ◎ |
| | HBr | 0.1 | | | | | | | | |
| Example 37 | HCl | 6 | 68.9 | 25 | 10 | 5 | 30 | 1 | 1.56 | ◎ |
| | HBr | 0.1 | | | | | | | | |
| Example 38 | HCl | 6 | 68.9 | 25 | 10 | 5 | 45 | 1 | 1.55 | ◎ |
| | HBr | 0.1 | | | | | | | | |
| Example 39 | HCl | 6 | 68.9 | 25 | 10 | 5 | 60 | 1 | 1.93 | ○ |
| | HBr | 0.1 | | | | | | | | |
| Example 40 | HCl | 6 | 68.9 | 25 | 10 | 5 | 75 | 1 | 2.39 | ○ |
| | HBr | 0.1 | | | | | | | | |
| Example 41 | HCl | 6 | 68.9 | 25 | 10 | 5 | 85 | 1 | 7.12 | ○ |
| | HBr | 0.1 | | | | | | | | |

TABLE 4

| | $M_aX_b$ | $M_aX_b$ Content (wt %) | Solvent Content (wt %) | HDCA Content (wt %) | Presence/ Absence of Cooling Unit | Current (A) | Time (h) | Temper- ature (° C.) | pH | Yield (%) | Amount of Electric Power per 1 g of ADCA (W/g) | ADCA Quality | Ratio of Br to Initial Introduction (%) |
|---|---|---|---|---|---|---|---|---|---|---|---|---|---|
| Example 42 | HCl HBr | 6 0.1 | 68.9 | 25 | ○ | 20 | 2.5 | 40 | 1 | 95 | 1.43 | ⊓ | 100 |
| Example 43 | HCl HBr | 6 0.1 | 68.9 | 25 | X | 20 | 2.5 | 40 | 1 | 95 | 1.43 | X | 25 |

In Table 4, in Example 43, in which a cooling unit was not included, it was confirmed that when the cooling unit was not included, the quality of ADCA was deteriorated, and the content of Br⁻ was significantly reduced compared to the content of initial introduction.

Examples 44 to 53

An azo compound was prepared in the same manner as in Example 1, but with changes as shown in Table 5 below.

Regarding the quality of the obtained ADCA described in Table 5 below, the meanings of the following indications are as follows.

⊡ : a decomposition temperature of about 207±0.5° C. (expression of an appropriate decomposition temperature)

○: a decomposition temperature of higher than about 207.5° C. to 209.5° C. or below (slightly higher than the appropriate decomposition temperature)

Δ: a decomposition temperature of higher than about 209.5° C. (decomposition is delayed and foaming ratio performance is lowered)

X: a decomposition temperature of lower than about 206.5° C. (a decreased quality of a foaming body due to premature foaming)

TABLE 5

| | $M_aX_b$ | $M_aX_b$ Content (wt %) | Solvent Content (wt %) | HDCA Content (wt %) | Current (A) | Relation Equation[1] (cm²/kg) | Time (h) | Temper- ature (° C.) | pH | Yield (%) | ADCA Quality | Exothermic property of electrode |
|---|---|---|---|---|---|---|---|---|---|---|---|---|
| Example 44 | HCl HBr | 6 0.1 | 68.9 | 25 | 10 | 0.1 | 5 | 40 | 1 | 85 | ⊓ | ○ |
| Example 45 | HCl HBr | 6 0.1 | 68.9 | 25 | 10 | 0.5 | 5 | 40 | 1 | 88 | ⊓ | ○ |
| Example 46 | HCl HBr | 6 0.1 | 68.9 | 25 | 10 | 1.0 | 5 | 40 | 1 | 95 | ⊡ | X |
| Example 47 | HCl HBr | 6 0.1 | 68.9 | 25 | 10 | 1.5 | 5 | 40 | 1 | 95 | ⊡ | X |
| Example 48 | HCl HBr | 6 0.1 | 68.9 | 25 | 10 | 2.5 | 5 | 40 | 1 | 95 | ⊓ | X |
| Example 49 | HCl HBr | 6 0.1 | 68.9 | 25 | 10 | 3.0 | 5 | 40 | 1 | 95 | ⊓ | X |
| Example 50 | HCl HBr | 6 0.1 | 68.9 | 25 | 10 | 6.0 | 5 | 40 | 1 | 95 | ⊡ | X |
| Example 51 | HCl HBr | 6 0.1 | 68.9 | 25 | 10 | 9.0 | 5 | 40 | 1 | 95 | ⊡ | X |
| Example 52 | HCl HBr | 6 0.1 | 68.9 | 25 | 10 | 12.0 | 5 | 40 | 1 | 96 | ⊡ | X |
| Example 53 | HCl HBr | 6 0.1 | 68.9 | 25 | 10 | 15.0 | 5 | 40 | 1 | 96 | ⊓ | X |

[1]The Relational Equation (1) is β/α, in which α is the weight of a first solution (kg), and β is the total contact area (cm²) of a negative electrode and a positive electrode in contact with the first solution.

In Table 5, in Examples 44 to 53, in which the contact area of the electrode per solution weight was changed, it was confirmed that when the contact area per solution weight is less than 0.8 cm²/kg, the yield was significantly reduced and heat was produced in the electrodes, thereby causing the decomposition of the azo compound and changes in quality and quality deterioration.

Comparative Example 2

The experiment was performed in the same manner as in Example 1, except that chlorine gas was directly introduced without electrolysis so as to synthesize an azo compound.

TABLE 6

| | $M_aX_b$ | $M_aX_b$ Content (wt %) | Solvent Content (wt %) | HDCA Content (wt %) | Current (A) | Time (h) | Temper- ature (° C.) | pH | Yield (%) | Content of ADCA Acquired (g) | ADCA Quality | Contentof Waste water Production (g of HCl per kg ADCA) |
|---|---|---|---|---|---|---|---|---|---|---|---|---|
| Example 33 | HCl HBr | 6 2 | 67 | 25 | 10 | 5 | 40 | 1 | 96 | 23.6 | ⊡ | None |
| Comparative Example 2 | Cl₂ | 15 | 75 | 25 | 10 | — | 40 | 1 | 94 | 23.1 | ○ | 627.8 g |

In Table 6, in Comparative Example 2, chlorine gas was directly introduced without performing an electrolysis reaction, and ADCA was obtained in a high yield of 94%, but it was confirmed that there were problems in that a large amount of chlorine source had to be continuously introduced, and 627.8 g of HCl was produced per 1 kg of ADCA but the HCl could not be reused, thus requiring wastewater treatment, and in that the HCl had to be neutralized using a large amount of an alkali compound for the wastewater treatment.

As described above, according to the embodiments of the present invention, it is possible to implement a device for producing an azo compound, in which it is not necessary to continuously introduce a chlorine source, etc. through a recycling process because a predetermined halogen compound ($M_aX_b$) is used, it can significantly reduce the burden of treatment of wastewater and by-products, and realize a high conversion rate and a high yield. Additionally, even if the electrolysis method is used, it is unnecessary to use a separator, and it is possible to implement a device for producing an azo compound capable of reducing electric power consumption compared to the conventional technology. Accordingly, the manufacturing process and process management can be easier, manufacturing cost can be reduced, and productivity can be improved.

In the present specification, preferred embodiments of the present invention have been disclosed. Although specific terms are used, these are only used in a general sense to easily describe the technical contents of the present invention and help the understanding of the present invention, but it is not meant to limit the scope of the present invention. It will be apparent to those of ordinary skill in the art to which the present invention pertains that other modifications based on the technical spirit of the present invention can be implemented, in addition to the embodiments disclosed herein. For example, those of ordinary skill in the art would be able to understand that the device for producing an azo compound according to the embodiments described with reference to FIGS. 2A to 5 and the method for producing an azo compound applying the same can be variously modified. Therefore, the scope of the invention should not be determined by the described embodiments, but should be determined by the technical ideas described in the claims.

REFERENCE NUMERALS

3A: reaction solution introduction unit
3B: hydrazo compound introduction unit
6: discharge unit
7: dehydration unit
8: dehydration mother liquor storage tank
9: recycling unit
10: vessel
11: negative electrode
12: positive electrode
13: separator
14: negative electrode compartment
15: positive electrode compartment
16: stirrer
20, 25: reaction tanks
35a, 35b: connecting pipes
45: pump
46: reaction solution transfer pump
55: electrode tank
60A, 65A: negative electrodes
60B, 65B: positive electrodes
70, 75: stirrers
85: gas treatment unit
17, 100: solutions
200A to 200E: reaction units
S10: first step
S20: second step
S30: third step
S40: fourth step

The invention claimed is:
1. A device for producing azo compound, comprising:
a reaction unit in which a first solution comprising a hydrazo compound and at least one type of $M_aX_b$ is contained;
a negative electrode disposed to be in direct contact with the hydrazo compound within the reaction unit;
a positive electrode disposed within the reaction unit so as to be in contact with the solution; and
a stirrer for stirring the first solution,
wherein:
X is a halogen element;
M is at least one selected from the group consisting of hydrogen, Li, Na, K, Mg, Ca, Mn, Fe, Ni, Cu, Ag, Zn, Sn, Zr, and Ti, or at least one selected from the group consisting of a primary ammonium ion, a secondary ammonium ion, and a tertiary ammonium ion; and
the a and b are each independently any one integer from 1 to 4, wherein all of the first solution, the negative electrode, the positive electrode, and the stirrer are disposed within the reaction unit, and wherein the stirrer is provided between negative electrode and the positive electrode, thereby being configured to stir the first solution that is in direct contact with both the negative electrode and the positive electrode.

2. The device of claim 1, wherein the device is configured to produce an $X_b$ molecule by electrolyzing the first solution, and to obtain a second solution comprising an azo compound, $M_aX_b$, and HX, wherein His hydrogen, by oxidizing the hydrazo compound with the $X_b$ molecule produced.

3. The device of claim 2, wherein the device further comprises a discharge unit connected to the reaction unit to discharge the second solution and separate a third solution comprising $M_aX_b$ and HX therefrom to thereby obtain a solid azo compound.

4. The device of claim 3, wherein the device further comprises a recycling unit connected to the reaction unit to re-introduce an additional hydrazo compound equivalent to the hydrazo compound and the third solution into the reaction unit.

5. The device of claim 2, wherein the device further comprises a gas treatment unit for capturing gas generated by electrolyzing the first solution, and the gas treatment unit is disposed at an upper end of the reaction unit.

6. The device of claim 1, wherein the $M_aX_b$ comprises at least one of a $Cl_2$ precursor and a $Br_2$ precursor.

7. The device of claim 1, wherein the negative electrode is configured to comprise stainless steel, titanium, aluminum, iron, copper, and Hastelloy, and an alloy or composite material comprising at least one of these.

8. The device of claim 1, wherein the positive electrode is configured to comprise titanium, Hastelloy, platinum, stainless steel, gold, silver, iridium, iridium-coated metal, ruthenium, chromium, nickel, manganese, iron, rubidium, or an oxide thereof, graphite, carbon lead, and an alloy or composite material comprising at least one of them; or configured to comprise at least one of an electrode where a noble metal is coated on a non-noble metal substrate, an electrode where a noble metal is coated on a non-metal substrate, and a composite-coated electrode of a metal oxide and platinum.

9. The device of claim 1, wherein the positive electrode and the negative electrode consist of multiple pairs.

10. The device of claim 1, wherein the reaction unit comprises:

a reaction tank in which the first solution is contained; and an electrode tank in which the positive electrode and the negative electrode are disposed.

11. The device of claim 10, wherein the device further comprises a pump for circulating the first solution within the reaction unit comprising the reaction tank and the electrode tank.

12. The device of claim 10, wherein the device further comprises a gas treatment unit, at an upper end of the reactor and the electrode tank, for capturing the gas generated by electrolyzing the first solution.

13. The device of claim 1, wherein the device further comprises a temperature control unit, which is provided inside or outside of the reaction unit, or as part of the reaction unit to control the internal temperature of the reaction unit.

14. The device of claim 1, wherein the device further comprises a cooling unit, which is provided inside or outside of the reaction unit, or as part of the reaction unit.

15. The device of claim 1, wherein the first solution, the negative electrode, and the positive electrode satisfy the following relational equation (1):

$$0.8 \leq \beta/\alpha \qquad \text{[relational equation (1)]}$$

wherein in relational equation (1), $\alpha$ is the weight of a first solution (kg), and $\beta$ is the total contact area ($cm^2$) of the negative electrode and the positive electrode in contact with the first solution.

\* \* \* \* \*